(12) United States Patent
Tsai et al.

(10) Patent No.: US 8,491,651 B2
(45) Date of Patent: Jul. 23, 2013

(54) INTRAOCULAR LENSES WITH INTERLENTICULAR OPACIFICATION RESISTANCE

(75) Inventors: Chi-Chun Tsai, Fort Worth, TX (US); Brett E. Thomes, Arlington, TX (US); Stephen J. Van Noy, Southlake, TX (US)

(73) Assignee: Novartis AG, Basel (CH)

( * ) Notice: Subject to any disclaimer, the term of this patent is extended or adjusted under 35 U.S.C. 154(b) by 189 days.

(21) Appl. No.: 12/874,863

(22) Filed: Sep. 2, 2010

(65) Prior Publication Data

US 2011/0060408 A1  Mar. 10, 2011

Related U.S. Application Data

(60) Provisional application No. 61/239,974, filed on Sep. 4, 2009.

(51) Int. Cl.
*A61F 2/16* (2006.01)

(52) U.S. Cl.
USPC ...................................................... 623/6.34

(58) Field of Classification Search
USPC ................... 623/6.16, 6.32, 6.34, 6.36, 6.56, 623/6.62
See application file for complete search history.

(56) References Cited

U.S. PATENT DOCUMENTS

| 5,420,213 | A | 5/1995 | Yang |
| 5,494,946 | A | 2/1996 | Christ et al. |
| 5,922,821 | A | 7/1999 | LeBoeuf et al. |
| 6,313,187 | B2 | 11/2001 | LeBoeuf et al. |
| 6,353,069 | B1 | 3/2002 | Freeman et al. |
| 6,703,466 | B1 | 3/2004 | Karakelle et al. |
| 7,033,391 | B2 | 4/2006 | Lai et al. |
| 7,071,244 | B2 | 7/2006 | Liao |
| 2006/0100703 | A1* | 5/2006 | Evans et al. .................. 623/6.37 |
| 2006/0206206 | A1* | 9/2006 | Peyman et al. .............. 623/6.34 |
| 2009/0076603 | A1* | 3/2009 | Avery et al. .................. 623/6.43 |

FOREIGN PATENT DOCUMENTS

| WO | 99/52570 | 10/1999 |
| WO | 2006/067638 | 6/2006 |

OTHER PUBLICATIONS

PCT International Search Report for corresponding PCT/US2010/047697 with mailing date Jan. 14, 2011.
PCT International Written Opinion for corresponding PCT/US2010/047697 with mailing date Jan. 14, 2011.
Werner L. et al., 2006, "Interlenticular opacification: Dual-optic versus piggyback intraocular lenses", J. Cataract and Refract. Surg, 32:655-661 [previously disclosed].
Werner Liliana, Mar. 2007, "Causes of intraocular lens opacification or discoloration", J. Cataract and Refract. Surg., 33(4):713-726.
Eleftheriadis H, Marcantonio J, et al., Interlenticular opacification in piggyback AcrySof intraocular lenses: explantation technique and laboratory investigations, Br. J. Ophthalmol. 2001, 85(7):830-836.

(Continued)

*Primary Examiner* — William H. Matthews
(74) *Attorney, Agent, or Firm* — Scott A. Chapple

(57) ABSTRACT

The present invention is directed to an intraocular lens, an intraocular lens system and a method of producing and/or implanting the lens or system in an eye wherein at least one intraocular lens includes a coating that aids in resisting interlenticular opacification (ILO). The material of the coating is preferably hydrophilic or super-hydrophobic.

15 Claims, 2 Drawing Sheets

OTHER PUBLICATIONS

Gayton JL, Apple DJ, Peng Q, et al., Interlenticular opacification: Clinicopathological correlation of a complication of posterior chamber piggyback intraocular lenses, J. Cataract Refract. Surg., 2000, 26:330-336.

Werner L., Mamalis N., et al., Interlenticular opacification: Dual-optic versus piggyback intraocular lenses, J. Cataract Refract. Surg., 2006, 32:655-661.

* cited by examiner

INTRAOCULAR LENSES WITH INTERLENTICULAR OPACIFICATION RESISTANCE

CROSS REFERENCE TO RELATED APPLICATION

This application claims priority under 35 U.S.C. §119 to U.S. Provisional Patent Application Ser. No. 61/239,974, filed Sep. 4, 2009, the entire contents of which are incorporated herein by reference.

TECHNICAL FIELD OF THE INVENTION

The present invention relates to an intraocular lens, an intraocular lens system and a method of producing and/or implanting the lens or system in an eye wherein at least one intraocular lens includes a coating that aids in resisting interlenticular opacification (ILO).

BACKGROUND OF THE INVENTION

The human eye functions to provide vision by transmitting and refracting light through a clear outer portion called the cornea, and further focusing the image by way of a lens onto the retina at the back of the eye. The quality of the focused image depends on many factors including the size, shape and length of the eye, and the shape and transparency of the cornea and lens.

When trauma, age, disease or other malady cause an individual's natural crystalline lens to become less transparent, vision deteriorates because of the diminished light which can be transmitted to the retina. This deficiency in the lens of the eye is often referred to as a cataract. The treatment for this condition is surgical removal of the natural crystalline lens and implantation of an intraocular lens (IOL).

While early IOLs were made from hard plastic, such as polymethylmethacrylate (PMMA), soft, foldable IOLs made from acrylate based material have become increasingly popular because of the ability to fold or roll these soft lenses and insert them through a smaller incision. Such acrylate based lenses are particularly desirable because they exhibit excellent folding and unfolding characteristics during and upon implantation within the eye. Such acrylate lenses also exhibit desired biocompatibility characteristics.

While typical procedures involve the implantation of only one lens in an eye, there are multiple situations where it is desirable to have a second or two lenses implanted. As one example, dual optic accommodative lenses have been developed to improve the focal range of IOLs. As another example, it may be desirable to, after insertion of a first IOL, implant a second IOL, referred to as piggyback lenses, to improve visual performance.

While such two lens systems can improve visual performance, recent articles have suggested that various types of these lens systems may be susceptible to the development of interlenticular opacification (ILO). Such articles include: Gayton J L, Apple D J, Peng Q, et al., *Interlenticular Opacification: A Clinicopathological Correction of a New Complication of Piggyback Posterior Chamber Intraocular Lenses*, J. Cataract Refract. Surg., 2000; Eleftheriadis H, Marcantonio J, et al., *Interlenticular Opacification in Piggyback AcrySof Intraocular Lenses: Explantation Technique and Laboratory Investigations*, Br. J. Ophthalmol. 2001, July 85(7): 830-836; and Werner L., Mamalis N., et al., *Interlenticular Opacification: Dual-Optic Versus Piggyback Intraocular Lenses*, J. Cataract Refract. Surg. 2006, 32: 655-661. At least one of these articles suggests that acrylate based two lens systems are susceptible to ILO formation.

In view of the above, it would be quite desirable to provide an intraocular lens, particularly a two lens system, that inhibits the formation of ILO that might otherwise occur.

SUMMARY OF THE INVENTION

In one embodiment, the present invention is directed to an intraocular lens for use as part of a set of dual optic intraocular lenses or piggyback intraocular lenses. The lens includes a body formed of a hydrophobic material and the body defines an outer surface. A coating is disposed on a region of the outer surface of the body. The coating is formed of a hydrophilic material or a super-hydrophobic material. The body and coating cooperatively form a first intraocular lens, which is configured to face and oppose an outer surface of a second intraocular lens when both the first and the second intraocular lens have been implanted within an eye.

In another embodiment, the present invention is directed to an intraocular lens system of dual optic intraocular lenses or piggyback intraocular lenses. The system includes a first intraocular lens having a body defining an outer surface and a coating disposed on a region of the outer surface of the body. The body of the first intraocular lens is formed of a hydrophobic material and the coating of the first intraocular lens is formed of a hydrophilic material or a super-hydrophobic material. The system also includes a second intraocular lens having a body defining an outer surface. The second intraocular lens is disposed adjacent the first lens thereby forming an interlenticular space between the first lens and the second lens. The coating of the first intraocular lens faces and opposes the outer surface of the second intraocular lens. Further, the coating of the first intraocular lens is located directly adjacent and at least partially defines the interlenticular space.

In yet another embodiment, the present invention is directed to a method of producing and/or implanting an intraocular lens system of dual optic intraocular lenses or piggyback intraocular lenses. According to the method, there is provided a first intraocular lens having a body defining an outer surface and a coating disposed upon a region of the outer surface. The body is formed of a hydrophobic material and the coating is formed of a hydrophilic material or a super-hydrophobic material. The first intraocular lens is implanted in an eye such that the first intraocular lens is disposed adjacent a second intraocular lens within the eye. The second lens also has a body defining an outer surface. The first and second lenses cooperatively form the intraocular lens system and the first and second lenses define an intralenticular space between the first and second lens. The coating of the first intraocular lens faces and opposes the outer surface of the second intraocular lens. Moreover, the coating of the first intraocular lens is located directly adjacent and at least partially defines the interlenticular space. The second lens may also have a coating formed of a hydrophilic or super-hydrophobic material and the coating of the second lens will typically face and opposed the coating of the first lens.

DETAILED DESCRIPTION OF THE INVENTION

The present invention is predicated upon the provision of at least one intraocular lens (IOL) and preferably two IOLs that have a coating for aiding in the prevention of opacification, particularly interlenticular lens opacification (ILO). The IOL [s] typically form an intraocular lens system such as a dual optic or piggyback lens system. The coating is typically formed of a hydrophilic or super-hydrophobic material for aiding in the resistance or prevention of ILO.

Unless otherwise specifically stated, percentages of materials as used herein are weight percentages (w/w).

Figure 1:
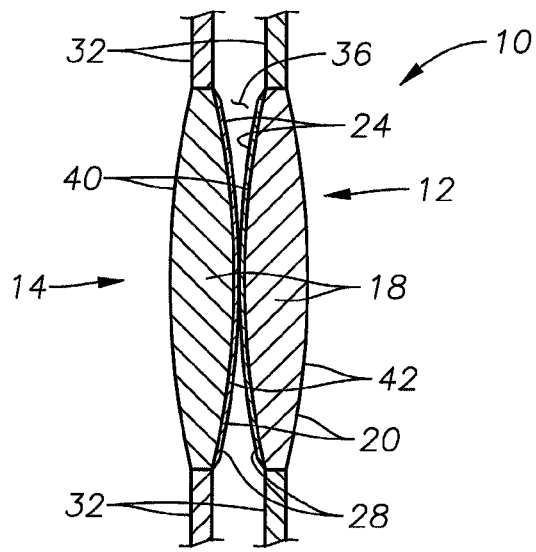
FIG. 1 is a sectional view of a pair of exemplary intraocular lenses that are arranged to form an intraocular lens system in accordance with an aspect of the present invention.

FIG. 1 illustrates an exemplary intraocular lens system 10 in accordance with an aspect of the present invention. The system 10 includes a first intraocular lens 12 and a second intraocular lens 14. As used herein, the terms "first" and "second" as they are used to indicate a lens of the system are merely used to indicate one of the lenses as opposed to the other. These terms are not intended to suggest any order such as order of implantation, unless otherwise specifically stated.

Each of the lenses 12, 14 includes a body 18 defining an outer surface 20 and a coating 24 disposed upon a region 28 of that outer surface 20. The coatings 24 of the lenses 12, 14 can aid in the prevention of ILO as is discussed further below. Each of the lenses 12, 14 also includes haptics 32 extending outwardly from the bodies 18 of the lenses 12, 14.

Each coating 24 of each of the lenses 12, 14 faces and opposes the outer surface 20 of the other of the lenses 12, 14. This is particularly the case after both lenses have been implanted within an eye. The intraocular lenses 12, 14 define an interlenticular space 36 therebetween and the coatings 24 of the lenses 12, 14 are both located directly adjacent and at least partially define the interlenticular space 36.

Figure 2:
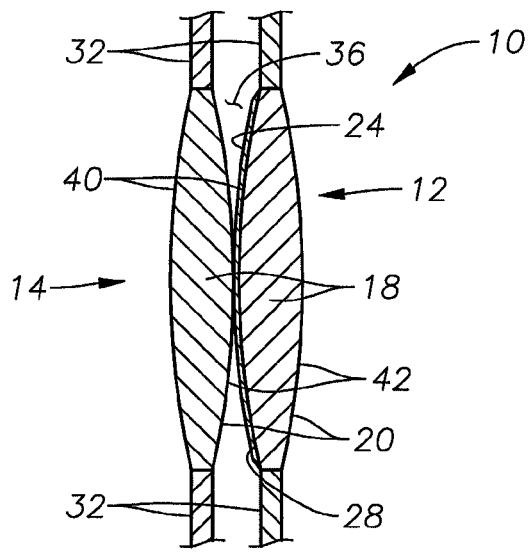
FIG. 2 is a sectional view of a pair of exemplary intraocular lenses are arranged to form an alternative intraocular lens system in accordance with an aspect of the present invention.

In the embodiment shown in FIG. 1, each of the lenses 12, 14 has its own coating 24. However, it is contemplated that only one of the lenses may have a coating while the other lens may be uncoated. This configuration is shown in FIG. 2. This may be the case, for example, when the intraocular system includes a set of piggyback lenses for which a first uncoated lens has already been implanted and a second coated lens is implanted as an adjustment to the first lens.

In the embodiment of FIG. 1, the coating 24 of each lens 12, 14 is disposed upon a region 28 of the body 18 and more particularly is disposed only upon one of two opposing sides 40, 42 of the body 18. It is contemplated, however, that the coating may be disposed upon other regions of the body or the entirety of the body of the lens. The term "region" as used herein is intended to mean only a portion of the body. However, the suggestion that the coating covers or is disposed upon a region of the outer surface of the body is not intended to restrict the coating from being located on other portions of the body unless it is specifically stated that the coating is only disposed upon that region.

In instances where the coating is selectively disposed upon only a region of the IOL, it is generally preferred that the region be a substantial portion of the outer surface of the body of the IOL. Preferably, that substantial portion is at least 20%, more preferably at least 40% and even possibly at least 60% of the outer surface of the body. The substantial portion is typically less than 90% and more typically less than 80% of the outer surface of the body. The aforementioned percentages are taken as percentages of total surface area of the body. The outer surface of the body is considered exclusive of any outer surface area of the haptics. Of course, the haptics may also be coated, but are not considered part of the body.

Figure 3:
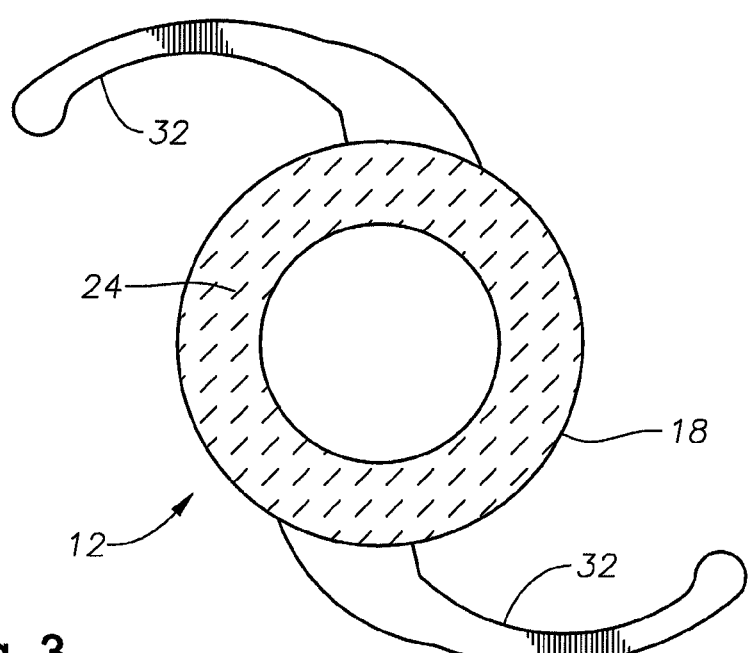
FIG. 3 is a front view of an exemplary intraocular lens in accordance with an aspect of the present invention.

In one preferred embodiment, the coating is formed as a ring about only a peripheral region of the IOL body as shown in FIG. 3. In such an embodiment, the peripheral region may be on only one side of the IOL or on both sides. It is contemplated that a second IOL in a system according to the present invention could have a ring shaped coating that is configured to oppose and face the ring shaped coating of FIG. 3 or such second IOL may have an alternative coating shape such as a coating covering one entire side of its body.

The body, the haptics or both of any of the intraocular lenses according to the present invention are preferably formed of a hydrophobic material. Such hydrophobic material will typically have a contact angle that is no greater than 90 degrees, more typically no greater than 85 degrees and even possibly no greater than 80 degrees. Such material will also typically have a contact angle that is at least 50 degrees and more typically at least 60 degrees and even possibly at least 65 degrees. Unless stated otherwise, contact angles for the materials of the present invention are determined in accordance with Young's equation as discussed in *Physical Chemistry of Surfaces* (*sixth edition*), Adamson, Arthur W. et al., Chapter X, pgs. 352-354.

The material of the body, the haptics or both is preferably an acrylate based material. Acrylate based materials are defined as having a substantial portion of acrylate monomers, which are preferably of formulation 1 below:

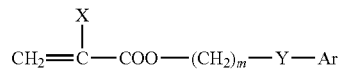

wherein: X is H or CH$_3$;
M is 0-10;
Y is nothing, O, S, or NR wherein R is H, CH$_3$, C$_n$H$_{2n+1}$(n=1-10), iso-OC$_3$H$_7$, C$_6$H$_5$, or CH$_2$C$_6$H$_5$;
Ar is any aromatic ring which can be unsubstituted or substituted with CH$_3$, C$_2$H$_5$, n-C$_3$H$_7$, iso-C$_3$H$_7$, OCH$_3$, C$_6$H$_{11}$, C$_6$H$_5$, or CH$_2$C$_6$H$_5$;

Suitable monomers of structure (I) include, but are not limited to: 2-ethylphenoxy methacrylate; 2-ethylphenoxy acrylate; 2-ethylthiophenyl methacrylate; 2-ethylthiophenyl acrylate; 2-ethylaminophenyl methacrylate; 2-ethylaminophenyl acrylate; phenyl methacrylate; phenyl acrylate; benzyl methacrylate; benzyl acrylate; 2-phenylethyl methacrylate; 2-phenylethyl acrylate; 3-phenylpropyl methacrylate; 3-phenylpropyl acrylate; 4-phenylbutyl methacrylate; 4-phenylbutyl acrylate; 4-methylphenyl methacrylate; 4-methylphenyl acrylate; 4-methylbenzyl methacrylate; 4-methylbenzyl acrylate; 2-2-methylphenylethyl methacrylate; 2-2-methylphenylethyl acrylate; 2-3-methylphenylethyl methacrylate; 2-3-methylphenylethyl acrylate; 24-methylphenylethyl methacrylate; 2-4-methylphenylethyl acrylate; 2-(4-propylphenyl)ethyl methacrylate; 2-(4-propylphenyl)ethyl acrylate; 2-(4-(1-methylethyl)phenyl)ethyl methacrylate; 2-(4-(1-methylethyl)phenyl)ethyl acrylate; 2-(4-methoxyphenyl)ethyl methacrylate; 2-(4-methoxyphenyl)ethyl acrylate; 2-(4-cyclohexylphenyl)ethyl methacrylate; 2-(4-cyclohexylphenyl)ethyl acrylate; 2-(2-chlorophenyl)ethyl methacrylate; 2-(2-chlorophenyl)ethyl acrylate; 2-(3-chlorophenyl)ethyl methacrylate; 2-(3-chlorophenyl)ethyl acrylate; 2-(4-chlorophenyl)ethyl methacrylate; 2-(4-chlorophenyl)ethyl acrylate; 2-(4-bromophenyl)ethyl methacrylate; 2-(4-bromophenyl)ethyl acrylate; 2-(3-phenylphenyl)ethyl methacrylate; 2-(3-phenylphenyl)ethyl acrylate; 2-(4-phenylphenyl)ethyl methacrylate; 2-(4-phenylphenyl)ethyl acrylate; 2-(4-benzylphenyl)ethyl methacrylate; and 2-(4-benzylphenyl)ethyl acrylate, and the like.

It is contemplated that the first and second IOLs of a system can be formed of substantially identical material, but may be formed of different materials. Preferably, the material of both IOLs of the system are acrylate based, however, it is possible for one to be acrylate based while another may be formed of a different material (e.g., a silicone based material). In such circumstances, the acrylate based IOL will typically include a coating according to the present invention while the other IOL of different material may or may not include a coating.

The material of the body and/or haptics is typically formed from at least 30%, more typically at least 70% and even possibly at least 95% acrylate monomers. The material of the body and/or haptics is typically formed from no greater than about 99.9% acrylate monomers. These acrylate based materials are typically mixed with a curing agent and/or a polymerization initiator so that the materials may be cured to form the IOLs. As such, it will be understood that these monomers are linked to form polymers in the finished IOLs. Examples of acrylate-based lenses are, without limitation, described in U.S. Pat. Nos. 5,922,821; 6,313,187; 6,353,069; and 6,703,466, all of which are fully incorporated herein by reference for all purposes.

The coating is preferably formed of a hydrophilic material or a super-hydrophobic material. A suitable hydrophilic material will typically have a contact angle that is no greater than 50 degrees, more typically no greater than 45 degrees and even possibly no greater than 35 degrees. Such material will typically have a contact angle that is at least 5 degrees.

A hydrophilic coating can also be formed of a hydrogel material. In such an embodiment, functionalized hydrogel precursors of hydrogel materials such as polyacrylic acid (PAA), polyvinyl acetate (PVA), polyvinyl pyrrolidone (PVP), polyethylene glycol (PEG), polyether imide (PEI), combinations thereof or the like may be coated upon the outer surface of the IOL body. The precursors can then be cross-linked by ultraviolet and/or visible light, plasma, radiation, heat energy or the like to form the coating of hydrogel material.

A suitable super-hydrophobic material for the coating will typically have a contact angle that is at least 90 degrees, more typically at least 100 degrees and even more possibly at least 130 degrees. Such material will typically have a contact angle no greater than 177 degrees.

When the coating is formed of a super-hydrophobic material, silicone based materials are typically quite desirable. Silicone based materials are those materials that include a substantial portion of silicon or silicon monomers (e.g., silane or siloxane). When silicone based, the material of the coating typically is formed from at least 30%, more typically at least 60% and even possibly at least 80% silicone monomers. In such embodiment, the material of the coating is typically formed from no greater than about 99.9% silicone monomers. Examples of silicone materials are, without limitation, described in U.S. Pat. Nos. 5,420,213; 5,494,946; 7,033,391; and 7,071,244, all of which are fully incorporated herein by reference for all purposes.

Silicone based coatings can be formed upon the body of the IOL using various techniques. In one embodiment, silicon monomers (e.g., silane or siloxane monomers) can be coated on the outer surface of the body by plasma deposition or polymerization onto the surface of the body. In another embodiment, plasma treatment (e.g., oxygen or water plasma treatment) can be employed to introduce hydroxyl groups onto the outer surface of the IOL body followed by a silanization treatment. In yet another embodiment, a surface modifying agent containing silicone block copolymer can be blended with the acrylate material prior to casting and curing of the IOL.

As an alternative to silicone, super-hydrophobic materials with even greater hydrophobicity (e.g., contact angles of at least 130 degrees) may be used. These super-hydrophobic coatings can be formed using continuous or, more preferably, modulated plasma deposition/polymerization treatment of perfluorocarbons monomers, which can then be cross-linked to form a polytetrafluoroehtylene (PTFE) coating. As an alternative, benzene moieties can be attached to the IOL body outer surface by direct fluorination to form a super-hydrophobic coating. As another alternative, plasma treatment (e.g., oxygen or water plasma treatment) can be used to introduce hydroxyl groups onto the outer surface of the IOL body followed by a fluorinated silanization treatment.

As an alternative or addition to a hydrophilic or super-hydrophobic coating, it is contemplated that a coating may be formed of bioactive agents. As one example, natural or synthetic molecules that modulate or inhibit protein adsorption and/or cell adhesion can be attached to the outer surface of the body to form a modified surface coating (e.g., a modified surface that preferentially adsorb serum albumin). As another example, pharmacological agents such as immunosuppressants, mTOR inhibitors or the like can be attached or otherwise coated on the outer surface of the IOL body to form a coating that prohibits or inhibits lens epithelial cell (LEC) growth. It is also contemplated that a coating may only cover a peripheral region (e.g., a peripheral edge) of the lens body and, for example, may form a ring about the lens body and/or may extend radially outwardly from the peripheral region. Still further, it is contemplated that the coating may be formed as a separate solid film (e.g., an annular disc shape film) that is then disposed over the surface of the lens body and preferably attached (e.g., adhered) thereto.

Implantation

Lens systems of the present invention can be implanted in the eye according various protocols. Typically a first lens is implanted followed by a second lens. It is contemplated, however, that two lenses may be implanted at least partially simultaneously. Both lenses may be implanted in the capsular bag or one may be located in the capsular bag while the other is outside of the capsular bag.

Figure 4:
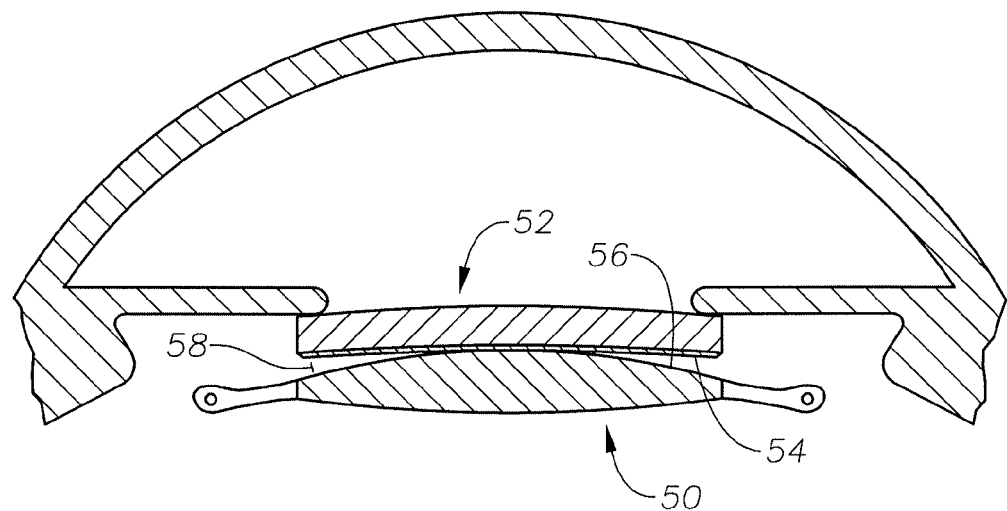
FIG. 4 is a sectional view of an exemplary piggyback lens system in accordance with the present invention.

In one preferred embodiment, a first lens is implanted in the capsular bag and then, upon discovery that the first lens is not providing the desired visual performance, a second lens is implanted in the sulces of the eye. Such lenses are typically referred to as piggy-back lenses. As example of such lenses are shown in FIG. 4. As can be seen, a first lens 50 is disposed in the capsular bag and is without a coating. However, a second lens 52, which has been implanted later in the sulces does include a coating 54 in accordance with the present invention. Generally, for piggy-back lens systems, the lens implanted in the sulces or the second lens implanted will be the only lens to include a coating since the lens in the capsular bag will have been implanted without the knowledge that a second lens would necessarily be implanted. Of course, it would be possible for the first implanted lens 50 (i.e., the lens in the capsular bag) to also include a coating, particularly if there is a likelihood that a second piggyback lens will be implanted later. In the embodiment shown, the coating 54 is in opposing facing relation to an outer side surface 56 of the first lens 50 and directly adjacent an interlenticular space 58 between the lenses.

Figure 5:
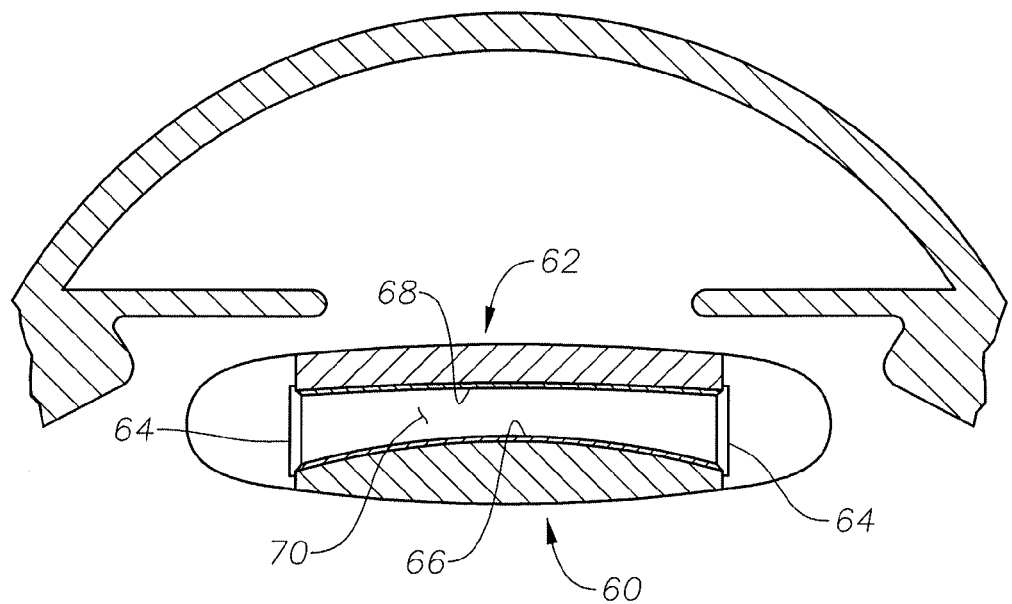
FIG. 5 is a sectional view of an exemplary dual optic accommodative lens system in accordance with the present invention.

In another preferred embodiment, a first lens is implanted in the capsular bag and then a second lens is implanted in the capsular bag and connected to the first lens to form a dual optic intraocular lens system (e.g., an accommodative system). As can be seen in FIG. 5, a first lens 60 having positive power is implanted and a second lens 62 having negative power is implanted. They are then attached to each other with attachment members 64 (e.g., interlocking haptics or other members) to form a dual optic accommodative intraocular lens system. As can also be seen, both of the lenses 60 and 62 having coatings 66, 68 on only one side of the lenses 60, 62 and those coatings 66, 68 are in opposing facing relation to each other and adjacent an intralenticular space 70.

The entire contents of all cited references in this disclosure are specifically incorporated herein by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An intraocular lens system comprising:
   a first intraocular lens that includes a body defining an outer surface and a coating disposed on a region of the outer surface of the body, the body of the first intraocular lens being formed of a hydrophobic material and the coating of the first intraocular lens being formed of a hydrophilic material or a super-hydrophobic material; and
   a second intraocular lens that includes a body defining an outer surface, the second intraocular lens being disposed adjacent the first lens thereby forming an interlenticular space between the first lens and the second lens, wherein:
   i) the coating of the first intraocular lens faces and opposes the outer surface of the second intraocular lens; and
   ii) the coating of the first intraocular lens is located directly adjacent and at least partially defines the interlenticular space: and
   attachment members connecting the first intraocular lens to the second intraocular lens as dual optic intraocular lenses;
   wherein the hydrophobic material has a contact angle that is at least 50 degrees but no greater than 85 degrees, the super-hydrophobic material has a contact angle that is at least 90 degrees and the hydrophilic material has a contact angle that is no greater than 45 degrees.

2. An intraocular lens system as in claim 1 wherein the second intraocular lens includes a coating formed of a hydrophilic material or a super-hydrophobic, material.

3. An intraocular lens system as in claim 2 wherein the coating of the second lens is located directly adjacent and at least partially defines the interlenticular space.

4. An intraocular lens system as in claim 1 wherein the coating of the first lens is disposed only on the region of the body leaving a substantial portion of the body uncovered by the coating.

5. An intraocular lens system as in claim 4 wherein the substantial portion is at least 60% of the surface of the body.

6. An intraocular lens system as in claim 1 wherein the hydrophobic material is an acrylate based material.

7. An intraocular lens system as in claim 1 wherein the coating is formed of a silicone based material.

8. An intraocular lens system as in claim 1 wherein the hydrophobic material has a contact angle that is at least 50 degrees but no greater than 85 degrees, the super-hydrophobic material has a contact angle that is at least 100 degrees, the hydrophilic material has a contact angle that is no greater than 35 degrees.

9. A intraocular lens system in claim 1 wherein the first intraocular lens and the second intraocular lens are formed of an acrylate based material.

10. An intraocular lens system as in claim 1 wherein the coating is formed of the super-hydrophobic material and the contact angle of the super-hydrophobic material is at least 100 degrees.

11. An intraocular lens system as in claim 1 wherein the coating is formed of the hydrophilic material and the contact angle of the hydrophilic material is no greater than 35 degrees.

12. An intraocular lens system as in claim 10 wherein the coating is a silicone based material formed from at least 60% silicone monomers.

13. An intraocular lens system as in claim 10 wherein the hydrophobic material has a contact angle that is at least 60 degrees but no greater than 80 degrees.

14. An intraocular lens system as in claim 11 wherein the hydrophobic material has a contact angle that is at least 60 degrees but no greater than 80 degrees.

15. An intraocular lens system as in claim 12 wherein the hydrophobic material has a contact angle that is at least 60 degrees but no greater than 80 degrees.

* * * * *